United States Patent [19]

Behl

[11] Patent Number: 5,078,736
[45] Date of Patent: Jan. 7, 1992

[54] METHOD AND APPARATUS FOR MAINTAINING PATENCY IN THE BODY PASSAGES

[75] Inventor: Robert S. Behl, Palo Alto, Calif.

[73] Assignee: Interventional Thermodynamics, Inc., Mountain View, Calif.

[21] Appl. No.: 519,383

[22] Filed: May 4, 1990

[51] Int. Cl.$^5$ .................. A61F 2/06; A61F 2/02
[52] U.S. Cl. ............................. 623/1; 623/66
[58] Field of Search ............... 623/1, 66; 128/642; 604/180; 606/198

[56] References Cited

U.S. PATENT DOCUMENTS

| | | |
|---|---|---|
| 3,983,581 | 10/1976 | Angell et al. . |
| 4,035,849 | 7/1977 | Angell et al. . |
| 4,202,331 | 5/1980 | Yale . |
| 4,580,568 | 4/1986 | Gianturco ............... 606/198 |
| 4,655,771 | 4/1987 | Wallsten ................. 623/1 |
| 4,665,906 | 5/1987 | Jervis . |
| 4,680,031 | 7/1987 | Alonso . |
| 4,699,611 | 10/1987 | Bowden . |
| 4,705,516 | 11/1987 | Barone et al. . |
| 4,767,411 | 8/1988 | Edmunds .................. 604/180 |
| 4,795,458 | 1/1989 | Regan . |
| 4,795,465 | 1/1989 | Marten . |
| 4,800,882 | 1/1989 | Gianturco . |
| 4,830,003 | 5/1989 | Wolff et al. . |
| 4,945,912 | 8/1990 | Langberg ................. 128/642 |

Primary Examiner—David J. Isabella
Attorney, Agent, or Firm—Townsend and Townsend

[57] ABSTRACT

An intraluminal stent for maintaining patency in body passages subject to invasive tissue growth includes a cylindrical wall having radial passages therethrough. A mechanism is provided for disrupting cellular growth which penetrates through the passages. The mechanism may provide for mechanical disruption, thermal disruption, or preferably for excision using radio frequency energy. In a specific embodiment, the cylindrical wall is defined by a tubular mesh, and the mechanism for disrupting cellular growth comprises parallel wires within the mesh. The wires are connected to an external radio frequency source and act as electrodes in effecting excision using the radio frequency energy.

25 Claims, 4 Drawing Sheets

METHOD AND APPARATUS FOR MAINTAINING PATENCY IN THE BODY PASSAGES

BACKGROUND OF THE INVENTION

1. Field of the Invention

The present invention relates generally to apparatus and methods for maintaining patency in body passages and, more particularly, to the construction and use of an intraluminal stent having the ability to periodically disrupt invasive tissue growth.

The occlusion of body passages is frequently a side effect of solid tumor growth. Such occlusion is often life threatening and almost always a cause of great discomfort to the patient. The most common method for reopening body passages which have been blocked by tumor growth has been surgical intervention where the occluding material is excised.

Surgical intervention, however, is undesirable due to the risk of post-operative complications.

Furthermore, the beneficial effect of such surgical intervention is frequently short-lived as regrowth of the tumor results in reocclusion of the body passage. Thus, it would be desirable to provide apparatus and methods which do not require major surgical intervention and which are able to maintain patency in the body passage for a longer period of time, preferably indefinitely.

The use of intraluminal stents to maintain patency in body passages subject to occlusion by invasive tumor growth has been proposed. See, for example, U.S. Pat. Nos. 4,699,611 and 4,580,658. The use of such stents, however, is problematic in several respects. The use of perforate stents, such as the mesh stents described in U.S. Pat. No. 4,580,658, frequently allows invasive tissue growth through the interstices in the wall of the stent. Thus, although the stent may inhibit the invasive growth for a time, reocclusion frequently occurs. Moreover, the presence of the stent enmeshed in the subsequent tumor growth can inhibit recanalization of the passage.

The tendency of perforate stents to allow reocclusion of the body passage can be overcome by the use of solid-wall stents, as described in U.S. Pat. No. 4,699,611. A solid wall can physically block the intrusion of the tumor cells into the lumen defined therein. Such solid-wall stents, however, also suffer from disadvantages. It is difficult to construct solid-wall stents which are expandable, so it is usually necessary to insert the stent in its full-sized configuration. (This is not true of mesh and other perforate stents which may be expanded to their final dimensions after being located within the body passage.) Solid-wall stents can also inhibit the supply of nutrients to and elimination of wastes from the tissue surrounding the body passage. Such blockage cannot only interfere with necessary bodily functions, but can also cause tissue necrosis which is undesirable in many circumstances. Finally, solid-wall stents are themselves subject to reocclusion as they tend to promote axial spreading of the tumor, which can block the lumen through the stent at either or both ends.

For these reasons, it would be desirable to provide improved apparatus and methods for maintaining patency within body passages subject to tumor growth. It would be particularly desirable if such apparatus and methods could inhibit reocclusion of the body passage without substantially inhibiting the normal exchange of nutrients and waste between said passage and the surrounding tissue. It would be further desirable if the apparatus and methods could be adapted to most or all body passages, including the urinary tract, the biliary tract, respiratory passages, pancreatic ducts, lymphatic ducts, and the like. The apparatus should be easy to implant (not requiring major surgery for implantation), and use of the apparatus should not result in release of viable tumor cells from the primary site being treated.

2. Description of the Background Art

The construction and use of stents which may be used to maintain patency in body passages subject to invasive tumor growth are described in U.S. Pat. Nos. 4,699,611; 4,580,568; and 4,800,882. U.S. Pat. Nos. 4,795,458 and 4,665,906, each disclose the use of heat to expand a stent within the body passage, usually a blood vessel. The stents are generally heated by an external source and do not possess or provide sufficient thermal energy to disrupt surrounding tissue growth. Other stent structures are disclosed in U.S. Pat. Nos. 4,830,003; 4,795,465; 4,705,516; 4,680,031; 4,655,771; 4,202,331; 4,035,849; and 3,983,581. Electrosurgery techniques employing bipolar radio frequency generators to deliver energy to electrodes for making surgical incisions are known.

SUMMARY OF THE INVENTION

The present invention comprises an apparatus and method for maintaining patency in body passages subject to occlusion by invasive tissue growth. The apparatus comprises an intraluminal stent having a generally cylindrical wall with a plurality of radially-disposed passages therethrough. The passages provide for the exchange of nutrients and wastes between an interior lumen in the stent and the surrounding tissue, allowing substantially normal growth and metabolism of the tissue without necrosis. Reocclusion of the lumen is prevented by a mechanism for intermittently disrupting tissue growth through the passages. The mechanism for disrupting tissue growth may be mechanical, but will more usually function by the controlled application of thermal and/or electrical energy. In particular, the stent may include resistive or inductive heating elements for thermally disrupting cell growth or may include radio frequency electrodes for disrupting cell growth using radio frequency energy. Electrical connections to the disrupting mechanism may be provided by a connector present on or beneath the skin surface or may be provided by inductive coupling.

The method of the present invention comprises positioning a stent within a body passage adjacent the region of excessive tissue growth. The stent can be introduced surgically, but will more usually be positioned transluminally, typically by using a transluminal catheter. Optionally, the stent may be expanded in situ in order to anchor the stent in the desired location. Once positioned, the surrounding tissue is allowed to grow through passages in the wall of the stent, but the tissue is periodically disrupted in order to prevent occlusion of the interior lumen of the stent. The use of thermal and radio frequency energy to disrupt the cellular growth is particularly advantageous as it inhibits the release of viable tumor cells.

DESCRIPTION OF THE SPECIFIC EMBODIMENTS

Figure 1:
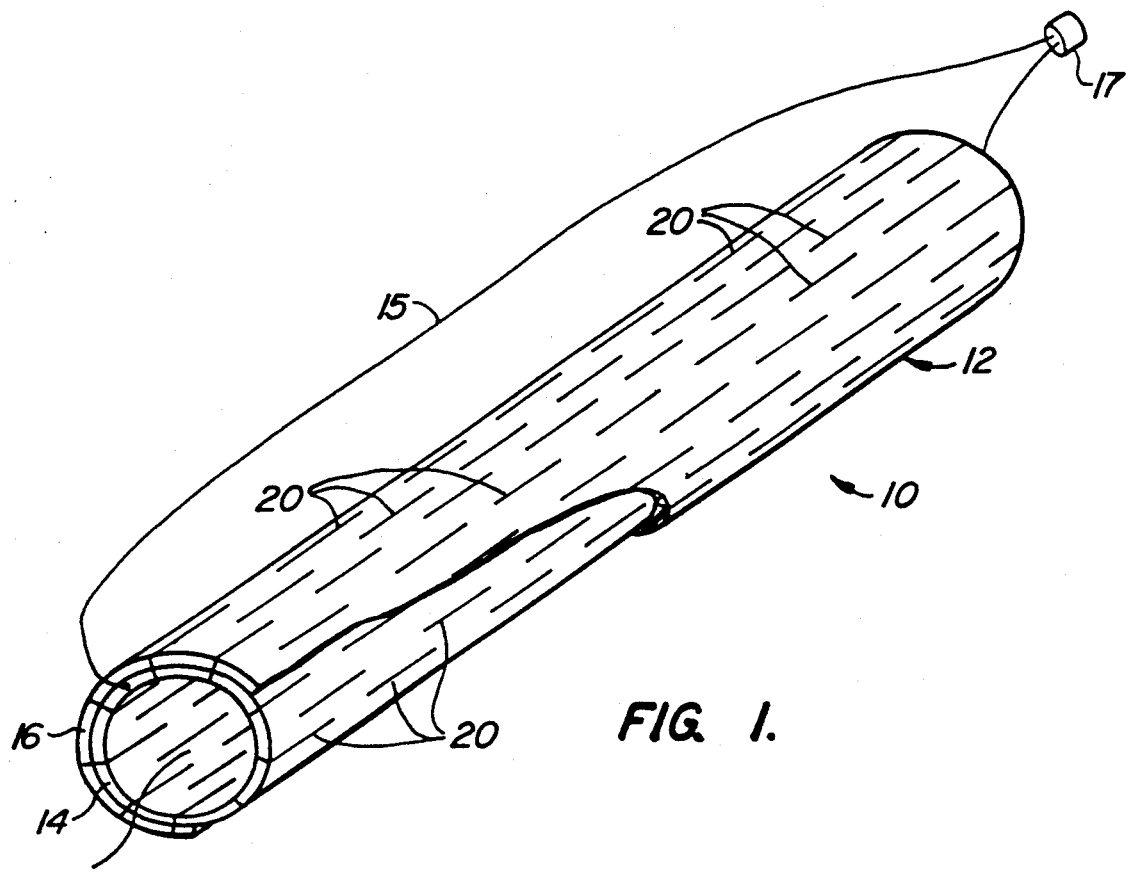
FIG. 1 is an isometric view of a first embodiment of an intraluminal stent constructed in accordance with the principles of the present invention.

The apparatus and method of the present invention may be used to open and maintain patency in virtually any hollow body passage which may be subject to occlusion by invasive cellular growth, particularly by invasive solid tumor growth. Suitable hollow body passages include ducts, orifices, lumens, and the like, with exemplary body passages including the ureter, the biliary ducts, respiratory passages, pancreatic ducts, lymphatic ducts, and the like.

The apparatus of the present invention comprises an intraluminal stent having a generally cylindrical wall structure which defines an internal lumen. The stent may be placed within a hollow body passage so that the cylindrical wall will inhibit invasive cellular growth and the lumen will maintain patency within the passage. A plurality of radial passages or apertures are formed through the cylindrical wall to allow substantially free exchange of nutrients, metabolites, wastes, and the like, between the body passage and the tissue surrounding the stent so that the tissue may continue to function and will not necrose. The radial passages further allow a controlled radially inward growth of cells which decreases the likelihood that invasive cell growth will extend to the axial ends of the lumen. As described in more detail hereinbelow, a mechanism is provided for periodically disrupting the tissue growth through the passages so that the patency of the lumen in the stent can be maintained for prolonged periods of time.

The structure of the cylindrical wall is not critical, with the only general requirement being the ability to direct the inward growth of tissue through the radial passages and to provide or support a mechanism for disrupting the directed cellular growth. Conveniently, the cylindrical wall will usually be in the form of a perforate tubular sheet where the radial passages are discrete perforations or in the form of a tubular mesh where the radial passages are the interstices within the mesh structure. It would also be possible to form the cylindrical wall as a porous membrane structure allowing diffusive cellular growth therethrough. It may be possible to construct the cylindrical wall from metals, organic polymers, inorganic polymers, composite materials, and the like. The nature of the materials of construction will depend largely on the type of mechanism used to disrupt cellular growth, as described in more detail hereinbelow.

Usually, the cylindrical wall will be expandable so that the stent may be inserted while in a collapsed or unexpanded configuration and expanded to a final desired size after placement within the body passage. This ability to expand in situ allows the stent to be placed within a partially occluded passage and thereafter be expanded to effect immediate opening of the passage. The expansion within the body passage further provides for anchoring of the stent so that it is less likely to become dislodged over time. Stents having a tubular mesh structure can easily be adapted to allow diametric expansion and contraction by axial compression and elongation. Stents formed from a perforate tubular sheet may be made expandable by initially forming the perforations as narrow, axial slits in the tubular wall. Diametric expansion of the tubular wall will then cause opening of the slits to the final desired dimension of the radial passages.

The dimensions of the cylindrical wall structure of the stent will vary depending on the desired use. Typically, the stent when in place in the body passage (after expansion, if appropriate) will have an axial length in the range from about 5 to 30 mm, more usually being in the range from about 10 to 15 mm, and a radial diameter in the range from about 2 to 5 mm, more usually being in the range from about 3 to 4 mm. The dimensions of the radial passages may also vary widely. When the passages are formed as discrete perforations in a sheet, they will typically have dimensions in the range from about 0.5 to 2 mm, more usually being in the range from about 0.8 to 1 mm. When the cylindrical wall is in the form of a mesh, the wires of the mesh will typically have a spacing in the range from about 0.5 to 2 mm, with a wire size in the range from about 0.1 to 0.5 mm. These dimensions, of course, are the final dimensions of the stent, and they may vary substantially if the stent is in an unexpanded configuration.

The cylindrical wall structure may optionally include further provision for anchoring the stent within the body passage, particularly in the case of non-expanding stent designs. For example, the cylindrical wall may include a cage structure which can be distorted after the main body of the stent is in place. See, for example, U.S. Pat. No. 4,699,611, the disclosure of which is incorporated herein by reference. Alternatively, the cylindrical wall may be attached to a variety of elements formed from shape-memory alloys, where the elements will return to an expanded configuration when the stent is in place. See, for example, U.S. Pat. Nos. 4,795,458 and 4,665,906, the disclosures of which are incorporated herein by reference. In addition, various pigtails, coils, and other discrete anchoring structures may be used for mechanically retaining the stent in place within the body passage in a manner well known in the art.

The intraluminal stent of the present invention will further include a mechanism for disrupting tissue growth which is secured to the cylindrical wall structure or formed as an integral portion of the cylindrical wall structure. The mechanism for disrupting tissue growth may be a simple mechanical device where tissue penetrating through the radial passages in the cylindrical wall is either cut or scraped away. The excised material will then be able to flow through the body passage and be disposed of by natural body processes.

A more desirable approach for disrupting the tissue growth through the radial passages will employ thermal ablation. Thermal ablation has advantages over mechanical disruption, including little or no bleeding, a reduced release of viable neoplastic cells, and a far less complex mechanical design. The most simple design for a thermally active stent will rely on an electrically conductive cylindrical wall structure, typically a metal wall structure, which can be inductively heated using a power source external to the patient. For such inductively heated stents, it will be desirable to provide thermal insulation surrounding the metal portion of the cylindrical wall structure. The thermal insulation will include radial passages corresponding to those in the electrically conductive portion of the wall. In this way, heating will be localized to the interior lumen surface of the cylindrical wall structure to minimize damage to the surrounding tissue of the body passage.

A thermally active stent can also be provided with a resistance heating element in the form of a single cylinder, a wire coil placed on the cylindrical wall, a plurality of axial elements, or the like. With each of these structures, it will be necessary to provide a means for connecting the resistance element to an external power source. Usually, connecting wires will be brought from the resistance element to a connector which is located just below the surface of the skin and accessed by a minor surgical incision. Alternatively, a coil could be formed beneath the surface of the skin and energy transferred to the coil inductively without requiring skin penetration.

The third and preferable alternative for disrupting tissue growth is the use of radio frequency energy to periodically excise tissue extending through the radial passages. The cylindrical wall structure will be provided with pairs of electrodes and means for connecting the electrodes to an external radio frequency energy source. The pairs of electrodes will be disposed on opposite sides of the radial passages so that the radio frequency energy will be directed precisely at the tissue which is growing into the lumen. In a preferred construction, the electrodes will be formed from parallel wires in a tubular mesh which forms the cylindrical wall structure. Such a design facilitates construction and reliability of the stent. Alternatively, the electrode pairs can be secured to the inner lumen surface of a perforate cylindrical wall. Connection of the electrodes to the external radio frequency source will typically be accomplished using a connector which is located just below the skin surface and may be accessed by minor surgical incision.

The intraluminal stents of the present invention may be introduced by a variety of known techniques, typically employing a specialty applicator or catheter which allows transluminal placement. Self-expanding mesh stents will typically be introduced using an ejector which constrains the diameter of the stent prior to ejection at the location of interest. See, for example U.S. Pat. Nos. 4,830,003; 4,655,771; and 4,580,568, the disclosures of which are incorporated herein by reference. Stents which are not self-expanding are typically delivered by balloon catheters which can actively expand the diameter of the stent after it has been delivered to the desired location. See, for example, U.S. Pat. No. 4,800,882, the disclosure of which is incorporated herein by reference.

Once in place in the body passage, the stent will be periodically actuated in order to disrupt tissue growth through the radial passages in the cylindrical wall structure. The frequency at which the stent is actuated will depend on the proliferation rate of the surrounding tissue, typically being actuated once every two to 10 weeks, more typically being actuated once every two to four weeks. Thermal ablation will be accomplished either by inductively heating a portion of the stent itself or by supplying current to a resistance heating element which is associated with the stent. Typically, heaters would be powered in the range from about 1 W to 10 W, more usually in the range from about 2 W to 5 W, will be provided for a period of time from about one to five minutes, more usually from about two to three minutes. Sufficient power should be supplied to heat the target tissue above its thermal damage threshold of about 42° C. to 45° C.

Radio frequency energy may be utilized either to coagulate the tissue penetrating through the radial passages or to excise the tissue. For coagulation, treatment will typically involve from about 5 W to 15 W of energy delivered using a coagulation waveform (damped sinusoidal) applied for up to about ten seconds. For excision, treatment will typically require from about 20 to 30 W of power using a cutting waveform (sinusoidal) for up to about one second.

Figure 2:
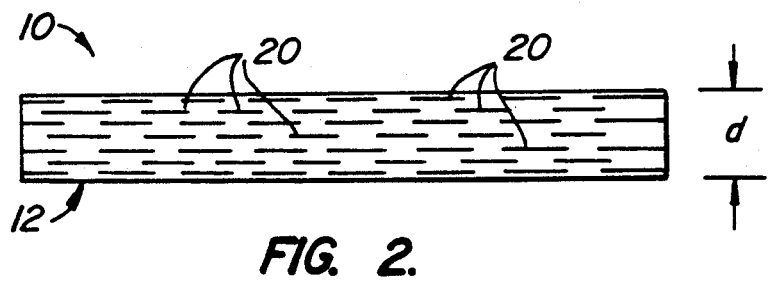
FIG. 2 is a side elevational view of the stent of FIG. 1, shown in its unexpanded configuration.
Figure 3:
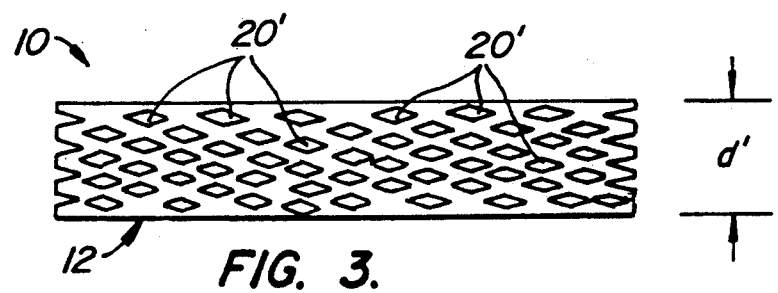
FIG. 3 is a side elevational view of the stent of FIG. 1, shown in its diametrically expanded configuration.

Referring now to FIGS. 1–3, a first embodiment 10 of the intraluminal stent of the present invention will be described. The stent 10 comprises a cylindrical wall 12 having an inner sleeve member 14 and an outer sleeve member 16. The inner sleeve member will be formed from an electrically conductive material, typically a metal, which may be heated inductively, or resistively from an external power source. For inductive heating, the inner sleeve 14 may be formed from virtually any electrically conductive material, such as stainless steel, gold alloy, and the like. For resistive heating, the inner sleeve 14 is preferably formed from a high-resistance metal, such as nickel-chrome alloy, nickel-iron alloy, and the like. Alternatively, the inner sleeve may be formed from a heat-conductive material, again typically a metal, and a separate wire heating coil (not shown) to be placed on the outer surface of the metallic sleeve.

In the case of resistive heating elements, a connecting wire 15 will be provided to allow for connection to an external current source. Conveniently, the wire 15 may terminate in a plug connector 17 which may be disposed at or beneath the patient's skin surface to allow for plug connection to a power source. Alternatively, an induction coil (not illustrated) may be provided on the wire connection 15. The induction coil may be disposed just beneath the surface of the patient's skin to allow for inductive coupling to a power supply.

The outer sleeve 16 will typically be formed from a thermally and electrically insulating material, such as a plastic or elastomer. The thermally insulating nature of outer sleeve 16 will protect the surrounding tissue from direct exposure to the heat generated by inner sleeve 14. In the structure of FIGS. 1–3, the inner sleeve 14 will typically provide the mechanical support for cylindrical wall 12, and the outer sleeve 16 need only be thick enough to provide the desired thermal protection.

Cylindrical wall 12 defines an internal lumen 18 which provides the desired flow-through capability for the stent 10. Cylindrical wall 12 further includes a plurality of axial slots 20 which extend through both the inner sleeve 14 and outer sleeve 16. The stent 10 is shown in its unexpanded configuration in FIGS. 1 and 2 where the cylindrical wall 12 has an external diameter d. In the unexpanded configuration, the slots 20 are usually very narrow and preferably substantially closed.

After cylindrical wall 12 is expanded to diameter d' (FIG. 3), the slots 20' will open to their desired final dimensions. As described above, expansion of the stent 10 will typically be accomplished using a balloon catheter (not illustrated) which is able to internally dilate the stent after it has been positioned at a desired location in the body passage.

Suitable materials for forming the outer layer 16 include silicone rubber, high-density polyethylene, polypropylene, and the like. These materials may be modified in various ways to increase their thermal insulation capacity. For example, hollow microspheres or foamed microbubbles may be incorporated within the structure of the layer in order to enhance resistance to heat transfer.

Figure 4:
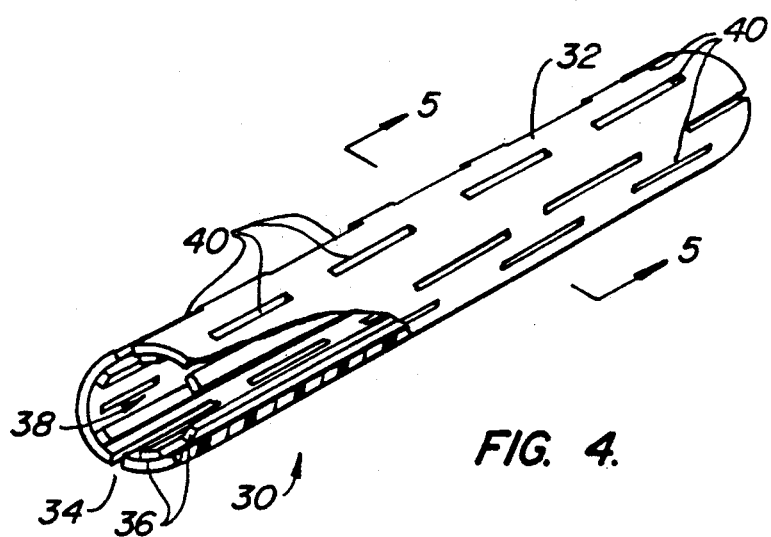
FIG. 4 is an isometric view of a second embodiment of an intraluminal stent constructed in accordance with the principles of the present invention.
Figure 6:
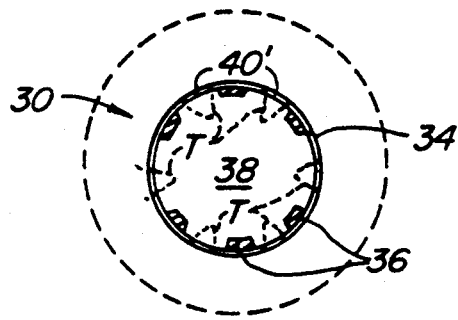
FIG. 6 is a cross-sectional view similar to that of FIG. 5, shown in an expanded configuration with open passages having tissue (illustrated in broken line) extending therethrough.
Figure 5:
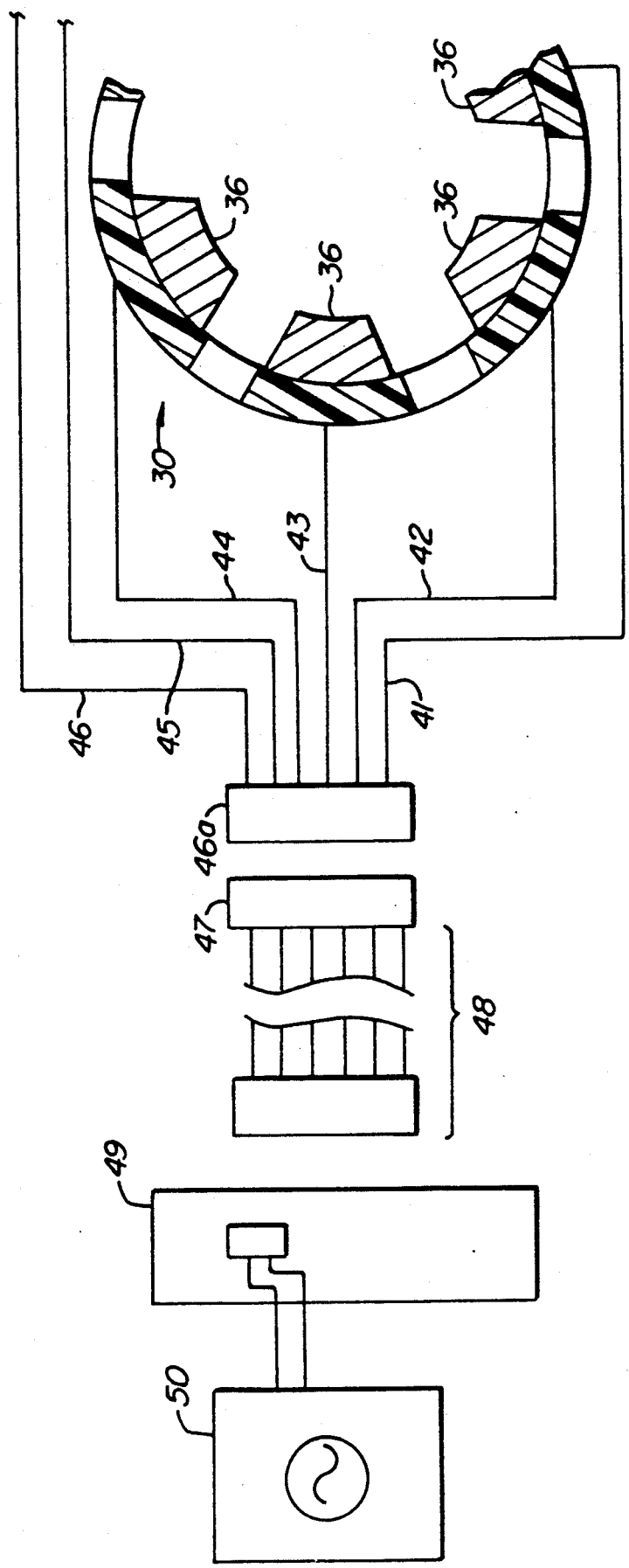
FIG. 5 is a cross-sectional view taken along line 5—5 of FIG. 4 and further illustrating the connection of internal electrodes within the stent to an external radio frequency source.

A second embodiment 30 of the intraluminal stent of the present invention is illustrated in FIGS. 4-6. The stent 30 comprises a cylindrical wall 32 which may consist of a single shell 34 composed of a deformable, electrically insulating material, such as nylon or polypropylene. A stent of this configuration would normally be compressed radially during insertion. Alternatively, the shell 34 may be composed of a malleable metal, such as stainless steel, which is coated with an electrically insulating material, such as tetrafluoroethylene (TFE) fluorocarbon polymers, fluorinated ethylene-propylene (FEP) resins, and the like. Such a configuration would normally require a radial dilation in situ, conveniently using a high pressure balloon catheter.

A plurality of electrodes 36 are disposed about an interior lumen 38 of the cylindrical wall 32. The electrodes 36 extend axially through the lumen 38 defining elongate axial regions therebetween. A plurality of slots 40 is formed through shell 34 and arranged axially so that they open into the regions between adjacent pairs of electrodes 36. In this way, each slot is bounded on either side by one of a pair of electrodes which can thus precisely direct radio frequency energy to tissue T (FIG. 6) penetrating through the slots 40.

The stent 30 is shown in its unexpanded configuration in FIG. 4 and in its expanded configuration in FIGS. 5 and 6. The slots 40 are illustrated as narrow openings when the stent 30 is in its unexpanded configuration. It will be appreciated, however, that the slots 40 could just as well be closed slots as shown above in connection with FIGS. 1 and 2.

FIG. 5 further illustrates a system for providing radio frequency energy to the electrodes 36. The system includes wire conductors 41, 42, 43, 44, 45, and 46 which are connected to individual electrodes 36. One conductor will be connected to each electrode 36. The wire conductors 41-46 are attached to a connector plug assembly 46a which will be located at or beneath the patient's skin. The connector 46a may be periodically attached to a mating connector 47 attached to an umbilical cable 48 which are maintained external to the patient's body. The cable 48 may then be attached to an electric pair selector switch 49 which in turn is connected to a bipolar radio frequency generator 50 of the type commonly employed in electrosurgery. Such generators are commercially available from suppliers such as Valleylab or Birtcher.

By powering adjacent electrodes 36 simultaneously (two at a time), the radio frequency energy is precisely directed to tissue T extending through expanded slots 40', as illustrated in FIG. 6. Individual conductors 41, 42, 43, 44, 45, and 46 and their respective electrodes 36 will typically be energized in an overlapping sequence, i.e., 41 and 42, 42 and 43, 43 and 44, 44 and 45, 45 and 46, 46 and 41, and so on, using the selector switch 49. The waveform, magnitude and duration of the radio frequency energy will be selected depending on whether coagulation or excision is desired. Precise selection of these factors is described generally above and is well within the skill of the art.

The electrodes 36 will typically be formed from a biocompatible metal, such as stainless steel, gold, platinum, or the like, with the particular material chosen based on the expected conditions encountered in the body passage. The electrodes 36 will typically be separated by a distance in the range from about 2 to 3 mm (after expansion), and it is necessary to assure that the path between adjacent electrodes is free from any highly electrically conductive material other than the tissue T extending in through the passages 40.

Figure 7:
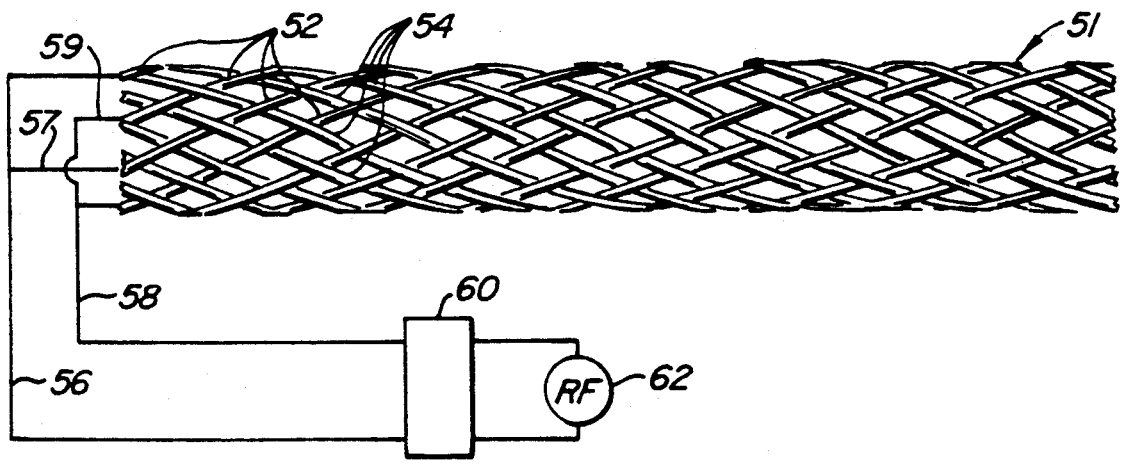
FIG. 7 is a side elevational view of a third embodiment of the intraluminal stent of the present invention.

Referring now to FIG. 7, a third embodiment 51 of the intraluminal stent of the present invention will be described. The stent 51 comprises a tubular mesh structure having a first plurality 52 of helical wires wrapped in a first direction and a second plurality 54 of helical wires wrapped in the opposite direction. The mesh structure of stent 51 will typically be self-expanding and anchoring and will be amenable to insertion using a conventional restraining catheter sheath or using a stylet or introducer which stretches the mesh structure to reduce its diameter. Use of stents formed from malleable wires allows an alternate method of placement of a small diameter stent which is permanently expanded (decreasing its length) in situ using a dilation balloon. General considerations relating to the construction and placement of such tubular mesh stents are described in detail in U.S. Pat. Nos. 4,580,586; 4,655,771; and 4,830,003, the disclosures of which have previously been incorporated herein by reference.

The stent 51 is intended for the administration of radio frequency energy to disrupt tissue growth which occurs through the interstices between adjacent pairs of wires. Conveniently, the first plurality of wires 52 may be formed from an electrically conductive metal suitable for use as an electrode, such as stainless steel. The second plurality of wires 54 will then be coated with an insulating material so that the individual wires 52 are electrically isolated from one another. Adjacent pairs of wires 52 are then connected to a radio frequency generator 62 using wire conductors 56-59 passing through a connector assembly 60, in a manner similar to that for stent 30 illustrated in FIGS. 4-6. Note that for ease of illustration, not all wire attachments are shown in FIG. 7. It is desirable that adjacent wire pairs be spaced apart by a preselected distance when the mesh is fully expanded, typically in the range from about 0.5 to 2 mm.

Figure 8:
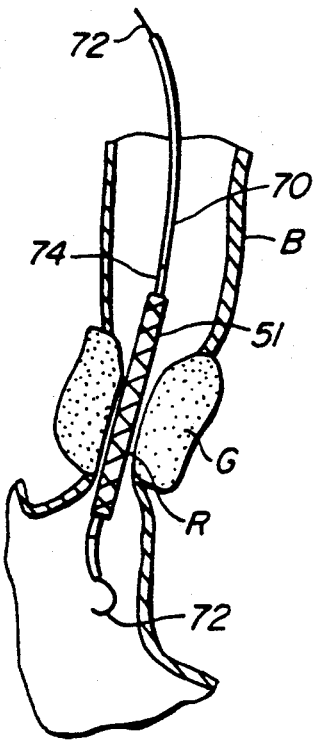
FIGS. 8-11 illustrate the method of the present invention for maintaining patency within a body passage employing a stent of the type illustrated in FIG. 7.
Figure 9:
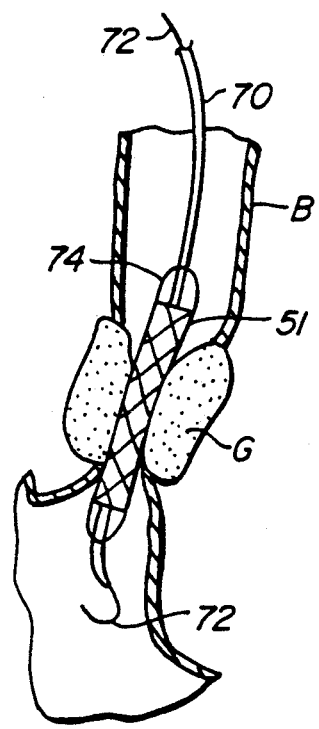

Referring now to FIGS. 8-11, a method for placing and utilizing the mesh-type stent 51 of FIG. 7 will be described. A biliary duct B subject to invasive growth from a tumor G is illustrated. The mesh stent 51 may be introduced within the restricted region R of the biliary duct B in a conventional manner using a balloon dilation catheter 70 positioned over a guide wire 72 (FIG. 8). After positioning catheter 70 so that stent 51 bridges the region R subject to invasive growth, a balloon 74 is inflated to expand the stent 51 so that it reopens the duct and is held in place via an interference fit (FIG. 9).

Figure 10:
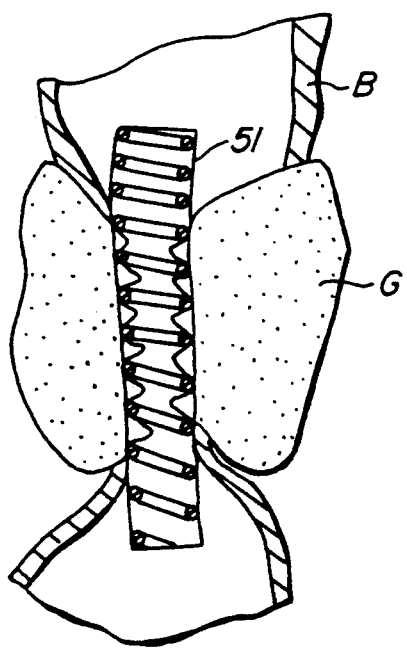
Figure 11:
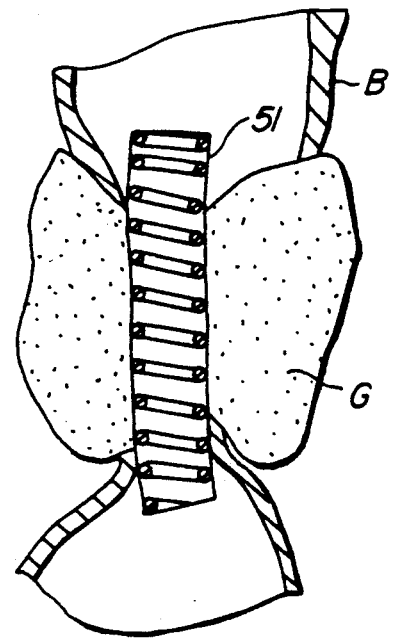

After a time, however, invasive growth of the tumor G will cause tissue to penetrate inward between the interstices of the mesh of stents 51, as illustrated in FIG. 10. Periodically, the electrode elements 52 of stent 51 may be excited with radio frequency energy in order to excise the cellular growth which penetrates between adjacent electrodes. In this way, the lumen defined by stent 51 may be periodically cleared of intruding cellular material, as illustrated in FIG. 11.

Although the foregoing invention has been described in detail for purposes of clarity of understanding, it will be obvious that certain modifications may be practiced within the scope of the appended claims.

What is claimed is:

1. A stent for maintaining patency in a body passage, said stent comprising:
   a generally cylindrical wall structure having apertures which allow tissue growth to penetrate therethrough; and
   means for intermittently applying energy directly to the stent to disrupt tissue growth penetrating through said apertures without substantial damage to tissue surrounding the wall structure.

2. A stent as in claim 1, wherein the cylindrical wall structure is expandable.

3. A stent as in claim 2, wherein the passages are slots which open as the cylindrical wall structure is expanded.

4. A stent as in claim 2, wherein the cylindrical wall structure is a mesh.

5. A stent as in claim 1, wherein the means for disrupting tissue growth includes an electrically conductive element which can be inductively heated and thermal insulation disposed over the exterior of said electrically conductive element.

6. A stent as in claim 1, wherein the means for disrupting tissue growth includes an electrically conductive element which can be resistively heated and thermal insulation disposed over the exterior of said electrically conductive element.

7. A stent as in claim 1, wherein the means for disrupting tissue growth includes pairs of electrically conductive spaced-apart elements located on opposite sides of the apertures in the cylindrical wall and means for coupling said pairs of elements to a radio frequency energy source.

8. A stent for maintaining patency in a body passage, said stent comprising:
   a generally cylindrical wall structure having apertures which allow tissue growth therethrough, said wall being electrically and thermally insulating; and
   means disposed on an interior lumen surface of the wall structure for supplying energy directly from the stent to disrupt tissue growth through said apertures.

9. A stent as in claim 8, wherein the cylindrical wall structure includes a plurality of generally axially aligned slots which allow diametric expansion of the wall and which define at least some of the passages when the wall is expanded.

10. A stent as in claim 8, wherein the means for applying energy comprises an electrically conductive sleeve which can be inductively or resistively heated.

11. A stent as in claim 10, wherein both the cylindrical wall structure and the electrically conductive sleeve include a plurality of generally axially aligned slots which allow diametric expansion of the wall and which define at least some of the passages when the wall is expanded.

12. A stent as in claim 8, wherein the means for applying energy includes pairs of electrically conductive spaced-apart elements and means for coupling said pairs of elements to a radio frequency energy source, wherein said spaced-apart elements are located on opposite sides of the apertures in the cylindrical wall.

13. A stent as in claim 12, wherein the pairs of electrically conductive elements are arranged generally axially on the internal lumen surface of the cylindrical wall structure.

14. A stent as in claim 10, wherein the means for coupling the conductive sleeve to an external power source comprises an inductive loop.

15. A stent as in claim 12, wherein the means for coupling the pairs of elements comprises a plug connector.

16. A stent for maintaining patency in a body passage, said stent comprising:
   a generally cylindrical mesh structure including multiple pairs of electrically conductive spaced-apart wires, wherein the wires of each pair are electrically isolated from each other; and
   means for coupling said pairs of spaced-apart wires to a radio frequency energy source, whereby energy is directed to tissue penetrating between said wires.

17. A stent as in claim 16, wherein the mesh is expandable.

18. A stent as in claim 17, wherein the mesh structure comprises a first plurality of resilient elements would helically in one direction and a second plurality of resilient elements would helically in the opposite direction, wherein at least some of the elements of one plurality form the electrically conductive wires and the elements of the second plurality are electrically insulated.

19. A stent as in claim 16, wherein the means for coupling the pairs of wires comprises a plug connector.

20. A method for maintaining patency in a body passage subject to occlusion resulting from excessive tissue growth, said method comprising:
   positioning a stent having a cylindrical wall structure within the body passage, said cylindrical wall having apertures therethrough;
   allowing tissue growth through said apertures in the cylindrical wall structure of the stent; and
   periodically applying energy directly to the stent to disrupt tissue growth through said apertures.

21. A method as in claim 20, wherein the stent is positioned within a body passage selected from the group consisting of the ureter, biliary duct, pancreatic duct, respiratory passages, and lymphatic duct.

22. A method as in claim 21, further comprising diametrically expanding the stent after positioning.

23. A method as in claim 20, wherein mechanical energy is applied to the stent.

24. A method as in claim 20, wherein heat energy is applied to the stent.

25. A method as in claim 20, wherein radio frequency energy is applied to the stent.

* * * * *